United States Patent [19]

Roden et al.

[11] Patent Number: 4,721,464

[45] Date of Patent: Jan. 26, 1988

[54] METHOD AND APPARATUS FOR MAKING A DENTAL MODEL

[76] Inventors: Mack L. Roden, 1095 Idlewood Dr.; Steven D. Adams, 3980 Midway Dr., both of Baker, Oreg. 97814

[21] Appl. No.: 745,481

[22] Filed: Jun. 17, 1985

[51] Int. Cl.[4] .................................. A61C 19/00
[52] U.S. Cl. ................................. 433/74; 433/34; 433/213
[58] Field of Search .................. 433/74, 213, 34; 264/16, 17, 18, 19, 225; 425/89

[56] References Cited

U.S. PATENT DOCUMENTS

| | | | |
|---|---|---|---|
| 1,780,117 | 10/1930 | Craigo | 433/74 |
| 2,091,072 | 8/1937 | Grant | 425/89 |
| 3,470,614 | 10/1969 | Kelly | 433/74 |
| 3,798,772 | 3/1974 | Eberhard | 433/74 |
| 3,937,773 | 2/1976 | Huffman | 433/74 |
| 4,078,310 | 3/1978 | Horger | 433/213 |
| 4,238,189 | 12/1980 | Tirino | 433/74 |
| 4,363,625 | 12/1982 | der Avanessian | 433/74 |
| 4,371,339 | 2/1983 | Zeiser | 433/74 |
| 4,398,884 | 8/1983 | Huffman | 433/213 |
| 4,443,192 | 4/1984 | Blitz | 433/74 |
| 4,449,931 | 5/1984 | Saito | 433/74 |

FOREIGN PATENT DOCUMENTS 1069355 1/1980 Canada .................. 433/74

Primary Examiner—John J. Wilson
Attorney, Agent, or Firm—Thomas W. Secrest

[57] ABSTRACT

This invention is directed to a means and a method for making a dental stone model. The NEGATIVE or impression of the teeth and gum of an individual is made as above described with respect to a yieldable material such as plastic, rubber and the like. After the NEGATIVE has been prepared the dowel and a parting guide are positioned in the NEGATIVE. The NEGATIVE is agitated and one pour of a pourable dental casting stone is made. The pourable dental casting stone surrounds the parting guide and almost all of the dowel pin. In time, the dental stone model or replica of the stub of the tooth is removed from the dental stone model by isolating the replica of the stub of the tooth. The parting guide allows the replica to be readily removed from the dental stone model. The dowel pin is an aligning means for the replica with respect to the dental stone model so that it is possible to position the replica of the stub of the tooth correctly in the dental stone model. The replica can be removed and also positioned again, numerous times, in the dental stone model without harm to the dental stone model.

37 Claims, 28 Drawing Figures

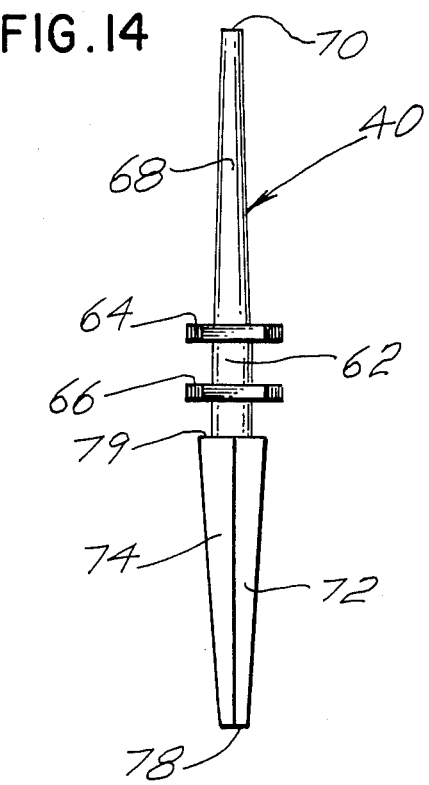
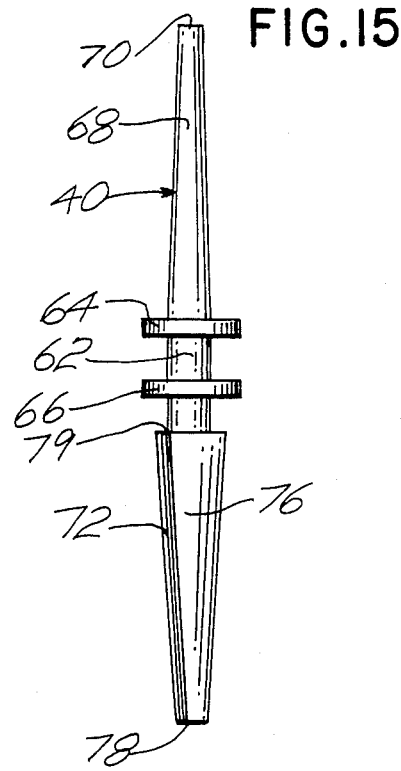
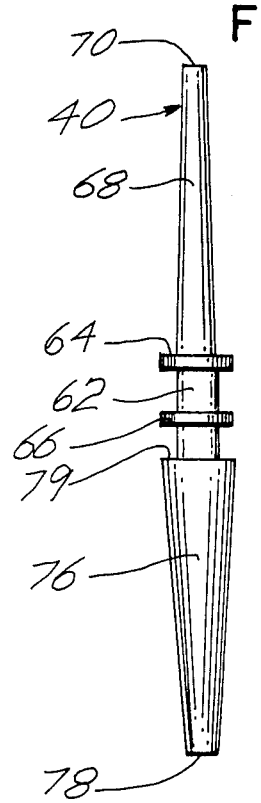
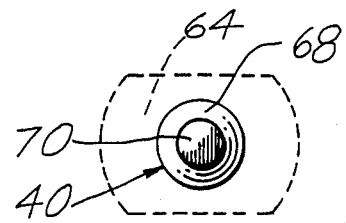
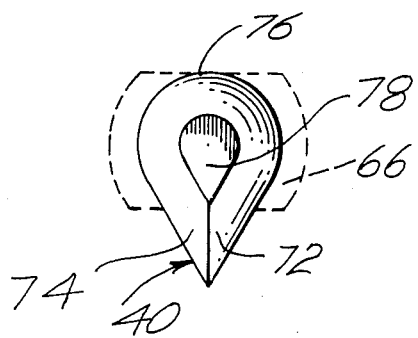

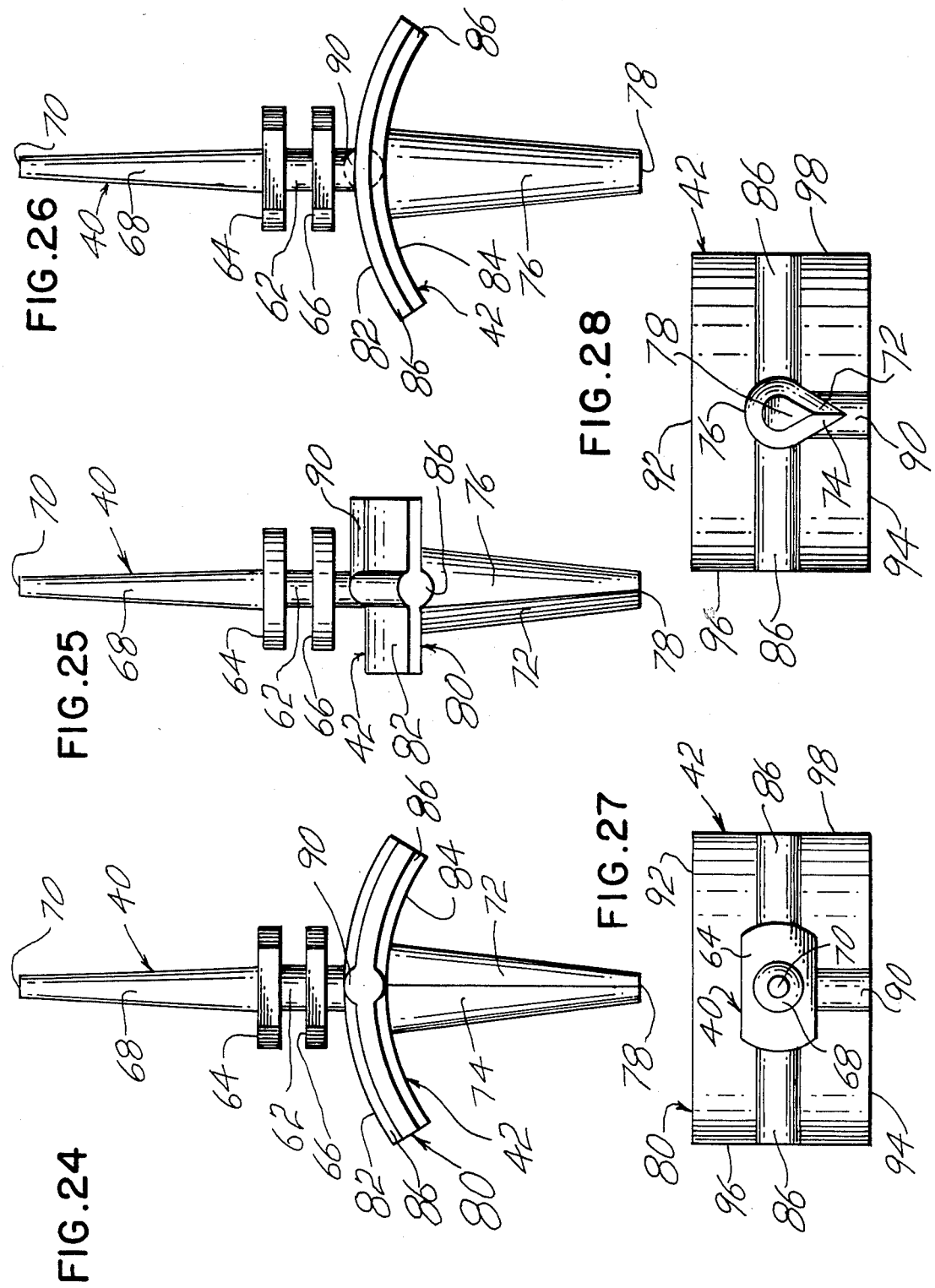

METHOD AND APPARATUS FOR MAKING A DENTAL MODEL

THE BACKGROUND OF THE INVENTION

This invention is directed to prosthetic dentistry.

Many people require repair or removal of teeth and the bridging of teeth. There is employed dental appliances such as jackets, crowns, inlays, onlays, bridges and combinations of these. To assist the dental technician in making the dental appliances there is often prepared a dental model of the mouth and teeth of an individual. The dental model may be of both the upper teeth and the lower teeth or the upper jaw and the lower jaw or the teeth and the lower jaw or the teeth and the upper jaw.

In the preparation of the dental models there is formed a NEGATIVE of the jaw or jaws of the individual. A yieldable material which will retain its shape and configuration after the individual bites into the yieldable material is used. The yieldable material may be a plastic or a rubber or a similar flexible material. The individual bites into this yieldable material and leaves recesses corresponding to the teeth and the gums.

For example, assume that an individual in the jaw has a full set of teeth but that one tooth needs a cap or a crown. The individual bites into the yieldable material to leave the impression of all the teeth and the jaw. The recess in the yieldable material will be more shallow for the stub of the tooth needing the crown or cap.

After the NEGATIVE has been formed in the yieldable material then a pourable dental casting stone is poured into the NEGATIVE. In time, say thirty (30) minutes to sixty (60) minutes, the pourable dental casting stone cures and hardens into the dental mold. The dental mold is removed from the NEGATIVE.

Then, the dental stone in the form of the stub of the tooth is isolated. The isolated dental stone in the configuration in the stub of the tooth is then used for preparing the cap or crown.

Over the years a number of techniques have been developed for making the dental model and also the dental stone model of the stub of the tooth. One technique is the Thompson method. In the Thompson method, in order to accomplish the removal of the dental stone replica of the stub of the tooth, two separate pourings of dental stone were poured into the NEGATIVE or the impression of the teeth and gum of the individual. It was necessary to have a separating material or a parting material between these two pourings of the dental stone. The Thompson technique often produced undesirable results because it failed to overcome the difficulty of initially freeing and separating the segment from the master model after the master model was hardened and removed from the NEGATIVE or impression of the teeth and gum. Also, the Thompson technique was time consuming and expensive.

One of the problems associated with the dental stone replica of the stub of the tooth is to position the dental stone replica into the dental stone model. The dental stone replica of the stub of the tooth can be removed from the dental model and then replaced. It is necessary to have an exact alignment of the dental stone replica of the stub of the tooth in the dental stone model so as to have a good and proper fit of the cap of the tooth. A patent to M. W. Kelly, U.S. Pat. No. 3,470,614, issuing date of Oct. 7, 1969 teaches of a method and an apparatus for making a dental model and also for positioning a protuberance 20 in the NEGATIVE and then a dowel pin 30 and a keying portion 40 on the dowel pin 30 in the NEGATIVE or the impression of the teeth and gum of an individual. A pourable dental casting stone is poured into the NEGATIVE and surrounds the dowel unit 30 and the keying portion 40. In time, the dental mold is removed from the NEGATIVE and the keying portion 40 and the dowel pin 30 are isolated and removed from the dental mold. The stub of the tooth surrounds the keying portion 40 and the dowel unit 30. The keying portion 40 of Kelly is wedged or firmly positioned in the NEGATIVE or in the impression of the teeth and gum of the individual.

A patent to Angelo C. Tirino, U.S. Pat. No. 4,238,189, issuing date of Dec. 9, 1980 teaches of positioning a divider and a pin in the NEGATIVE. The pourable dental casting stone is poured into the NEGATIVE and surrounds the divider and also the pin. After the casting stone has cured into the dental model the stub of the tooth can be isolated and separated from the dental model to assist in preparing the crown or cap.

There are two patents to Ronald E. Huffman, U.S. Pat. No. 3,937,773 issuing date of Feb. 10, 1976 and also U.S. Pat. No. 4,398,884 issuing date of Aug. 16, 1983. These patents teach of positioning a retainer in the NEGATIVE and making two dental pours. The retainer has recesses or passageways for receiving an aligning pin. Then, the second pour can be made around the upper part of the aligning pin. After the dental stone has cured and hardened the stub of the tooth can be isolated for further work in preparing the crown or cap.

The foregoing comments with respect to isolating and separating the stub of the tooth for use in preparing a crown or a cap is also applicable in regard to preparing a bridge, a jacket and the like.

THE GENERAL DESCRIPTION OF THE INVENTION

This invention is directed to a means and a method for making a dental stone model. The NEGATIVE or impression of the teeth and gum of an individual is made as above described with respect to a yieldable material such as plastic, rubber or the like. After the NEGATIVE has been prepared a dowel and a parting guide are positioned in the NEGATIVE. The NEGATIVE is agitated and one pour of a pourable dental casting stone is made. The pourable dental casting stone surrounds the parting guide and almost all of the dowel pin. In time, the dental stone model or replica of the stub of the tooth is removed from the dental stone model by isolating the replica of the stub of the tooth. The parting guide allows the replica to be readily removed from the dental stone model. The dowel pin is an aligning means for the replica with respect to the dental stone model so that it is possible to position the replica of the stub of the tooth correctly in the dental stone model. The replica can be removed and also positioned again, numerous times, in the dental stone model without harm to the dental stone model.

THE DRAWINGS

In the drawings it is seen:

FIG. 14 is a first side elevational view of the dowel pin;

FIG. 15 is a second side elevational view of the dowel pin;

FIG. 16 is a side elevational view of the dowel pin;

FIG. 17 is a top plan view of the dowel pin;

FIG. 18 is a bottom plan view of the dowel pin;

FIG. 24 is a first end elevational view of the combination of the dowel pin and the guide;

FIG. 25 is a side elevational view of the combination of the dowel pin and the guide;

FIG. 26 is a second end elevational view of the dowel pin and the guide;

FIG. 27 is a top plan view of the dowel pin and the guide; and,

FIG. 28 is a bottom plan view of the dowel pin and the guide.

THE SPECIFIC DESCRIPTION OF THE INVENTION

Figure 1:
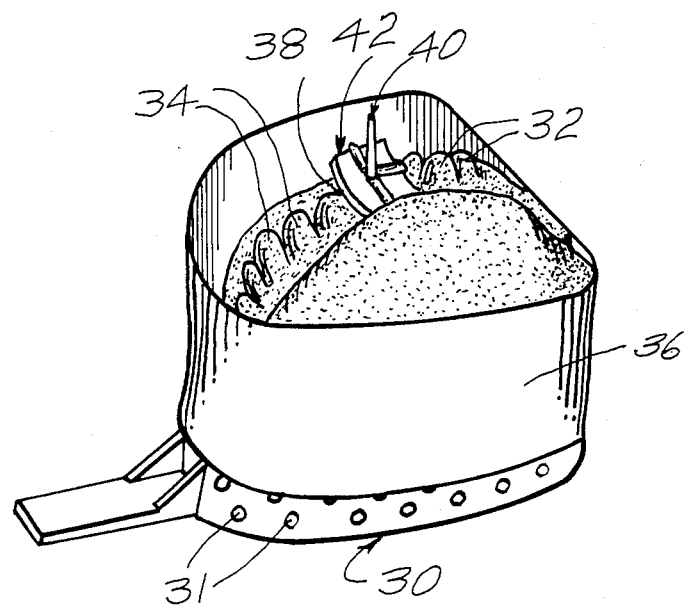
FIG. 1 is a top fragmentary axonometric view showing the impression tray and the impression of the tooth and a plastic mastic and the combination of a pin and a guide in the impression of one of the teeth and also illustrates the skirt around the upper part of the impression tray and above the plastic mastic and prior to receiving the liquid uncured dental stone.

It is seen that in the drawings that there is a dental impression tray 30. This dental impression tray is commercially available. One readily available tray 30 is of plastic and has a number of holes or passageways 31.

There is positioned on the tray 30 a yieldable mastic 32. The mastic 32 is positioned on the upper surface of the tray 30 and may be one of many suitable materials such as a hydrocolloid, rubber, a thermal plastic material or other similar flexible material.

The combination of the tray 30 and yieldable mastic 32 are inserted into the mouth of the dental patient. The dental patient bites into the yieldable mastic 32 to leave impressions 34 of his or her teeth and gums.

The tray 30 and the yieldable mastic 32 with the impressions 34 of the teeth and gums are removed from the mouth of the dental patient and allowed to cure and harden into a rigid solid material.

Then, a dam 36 is constructed around the dental impression tray and the mastic having the impressions 34 of the dental patient's oral jaw.

There is a recess 38 corresponding to a tooth of the dental patient.

A dowel pin 40 is inserted into the recess 38. A parting guide 42 is positioned around the dowel pin 40. The parting guide 42 is spaced a short distance, say one quarter of an inch, from the yieldable mastic 32.

A flowable uncured dental stone 44 is poured into the negative of the dental patient's oral jaw so as to cover the impressions 34 and also to be contained inside of the dam 36. While pouring the flowable uncured dental stone 44 into the negative of the dental patient's oral jaw the dental tray 30 and the yieldable mastic 32 are gently agitated The agitation is to try and have an even flow of the uncured dental stone into the impressions 34 and also around the dowel pin 40 and also to cover the parting guide 42. It is advisable that the end of the dowel pin 40 be above the uncured dental stone or to project above the uncured dental stone.

The uncured dental stone is allowed to cure for about thirty minutes to form a hard solid castmodel of the dental patient's oral jaw and also a replica gum of the gum of said dental patient's oral jaw and a model tooth being a replica of a tooth of said dental patient.

Figure 2:
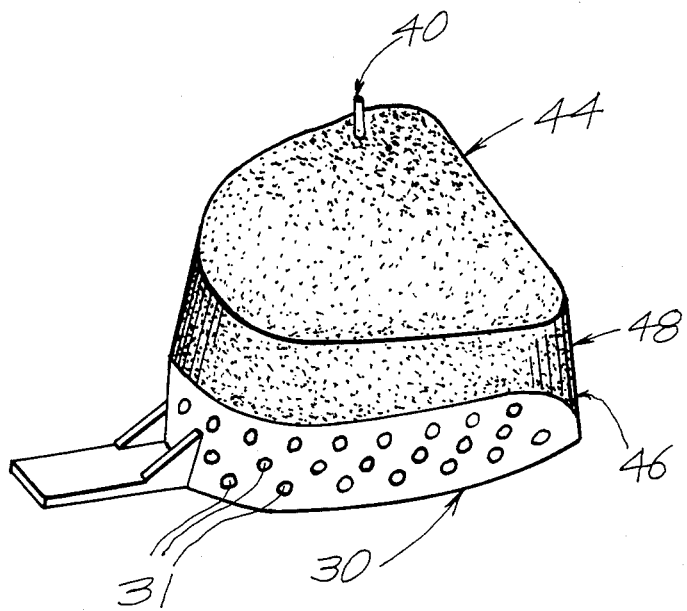
FIG. 2 is a top fragmentary axonometric view showing the impression tray with the hardened and cured dental stone on top of the impression tray and also illustrates part of the dowel pin projecting above the dental stone.

In FIG. 2 it is seen that there is a combination 46 of the dental impression tray 30 and the cured dental stone castmodel 48. The dam 36 has been removed. The cured dental stone castmodel 48 is sufficiently strong that it is no longer necessary to have the dam 36. Also, it is seen that there is mastic 32 in the holes 31 in the dental impression tray 30.

Figure 3:
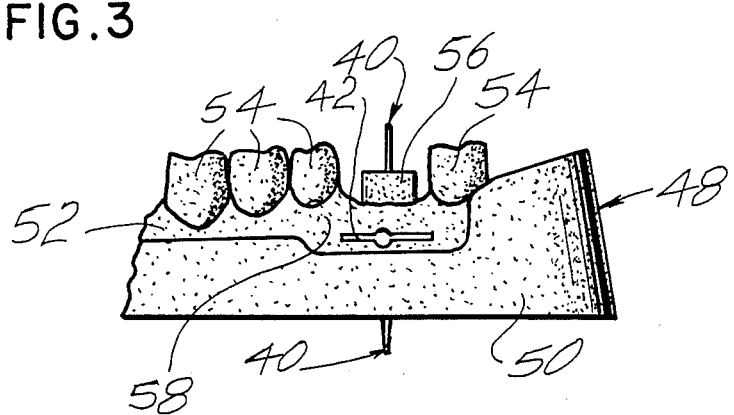
FIG. 3 is a side elevational view of the dental stone impression as corresponding to the teeth of an individual and shows part of the dental stone removed and cut away to illustrate plastic in the dental stone and also both ends of the dowel pin and also illustrates the stub of the tooth.

In FIG. 3 there is illustrated the castmodel 48 having a base 50 and gum 52. There are models 54 of teeth. Reference numeral 56 refers to the model tooth in the dental patient's oral jaw. Reference numeral 58 is for the buccal wall of the gum 52. Also, it is seen that part of the base 50 and the gum 52 in the vicinity of the model tooth 56 have been removed to show the outside edge of the parting guide 42. There is a dowel pin 40 in the base 50, the gum 52 and the model tooth 56. Also, the dowel pin 40 extends outside of the base 50 and also extends outside of the model tooth 56.

Figure 4:
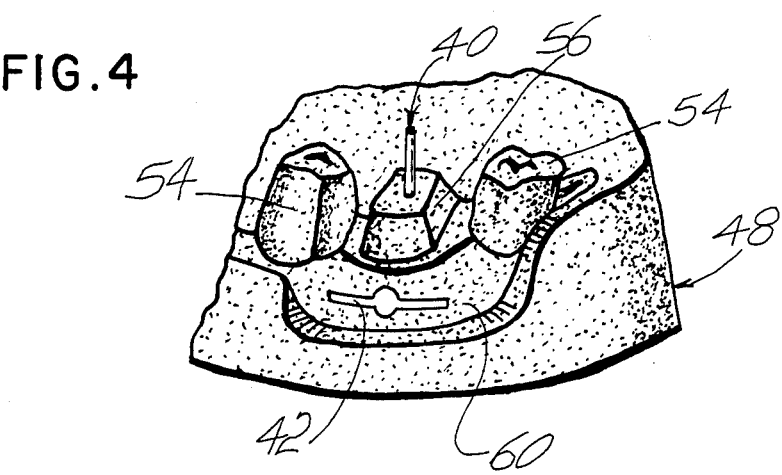
FIG. 4 is a top fragmentary axonometric view showing the dental stone impression of the teeth of an individual and illustrates the stub tooth, part of the dental stone removed in the vicinity of the stub tooth, the plastic in the dental stone and underneath the stub tooth and also part of the dowel pin.

In FIG. 4 there is illustrated the castmodel 48 and looking at the lingual wall 60 of the gum 52. There is illustrated the base 50 and the gum 52 and the model 54 of teeth. Again, reference numeral 56 refers to the model tooth in the dental patient's oral jaw. Part of the base 50 and the gum 52 have been removed in the vicinity of the model tooth 56 to expose the inside edge of the parting guide 42. Further, the dowel pin 40 is seen as extending outside of the model tooth 56.

In FIGS. 14, 15, 16, 17 and 18 there is illustrated the dowel pin 40 having a shank 62 or middle part 62. There are two spaced apart circumscribing ridges 64 and 66 on the shank 62. That end of the dowel pin 40 connecting with the circumscribing ridge 64 is a tapering end 68 terminating in a flat end 70. The tapering end 68 is in the configuration of a frustrum of a cone.

On that end of the shank 62 closer to the circumscribing ridge 66 there are two flat sides or flat faces 72 and 74 joined by a curved part 76. On the outer end there is a flat end 78.

In FIGS. 24, 25, 26, 27 and 28 there is an illustration of the combination of the dowel pin 40 and the parting guide 42. The parting guide 42 comprises a sheet 80 having a convex surface 82 and a concave surface 84 On the convex surface 82 there is a raised central longitudinal quide 86. On the concave surface 84 there is a raised central longitudinal guide 88. There is a central half lateral guide 90 which extends above the convex surface 82 and also extends above the concave surface 84.

It is seen that the parting guide 42 is in a genrally rectangular configuration having opposed sides 92 and 94 and opposed ends 96 and 98. The raised central longitudinal guides 86 and 88 extend from the end 96 to the end 98. The central half lateral guide 90 extends from the central longitudinal guides 86 and 88 to the side 94.

The dowel pin 40 projects through the parting guide 42 and with the parting guide 42 positioned between the circumscribing ridge 66 and the inner ends of the two flat face 72 and 74 and the curved part 76 identified by ridge 79. The ridge 79 is defined by the inner edges of the two flat faces 72 and 74 and the curved part 76.

The dowel pin 40 can be made of metal or can be made of plastic. In many repsects a plastic is preferable to a metal. It is easier to remove that part of the dowel pin which extends beyond the model tooth 56 if the dowel pin be of plastic instead of metal. Also, a plastic dowel pin can be prepared at less cost than a metal dowel pin.

In FIGS. 19, 20, 21, 22 and 23 there is illustrated the parting guide 42.

The parting guide 42 can be of plastic. The dental stone 44 does not readily adhere to plastic. The parting guide 42 can be positioned on the dowel pin 40 between the circumscribing ridge 66 and the ridge 79. There may be a central hole 99 or cut in the parting 42 so that the guide end of the dowel pin 40 with the two flat faces 72 and 74 and the curved face 76 can be pushed through the hole 99 or cut so that the parting guide is pushed to bear against the surface of the circumscribing ridge 66.

Figure 5:
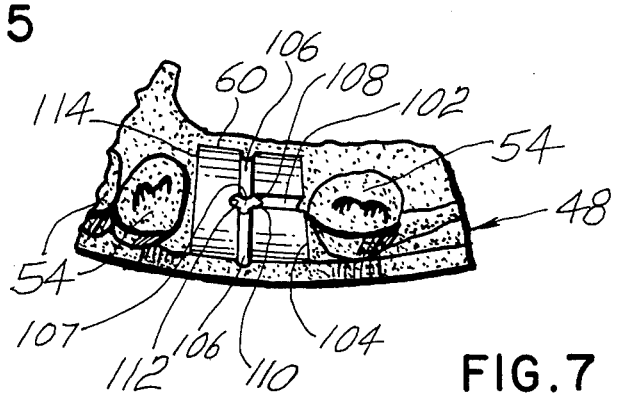
FIG. 5 is a top plan view of the dental stone with the stub of the tooth cut away and also illustrates the guide for the stub of the tooth and the hole in the dental stone for receiving the dowel pin for positioning the stub tooth in the dental stone.
Figure 6:
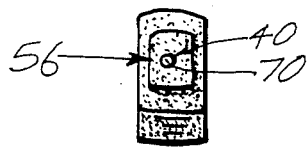
FIG. 6 is a top plan view of the stub of the tooth, actual size, after it has been removed from the dental stone and also illustrates the dowel pin.
Figure 7:
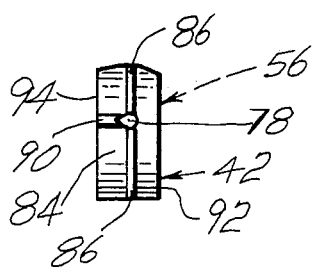
FIG. 7 is a bottom plan view of the stub of the tooth, actual size, and the guide for aligning the stub of the tooth in the dental stone and also illustrates the dowel pin.
Figure 8:
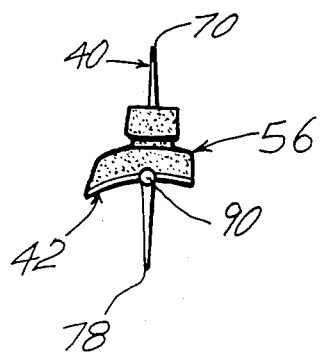
FIG. 8 is a side elevational view of the stub of the tooth after it has been removed from the dental stone, actual size, and illustrates the dowel pin.
Figure 9:
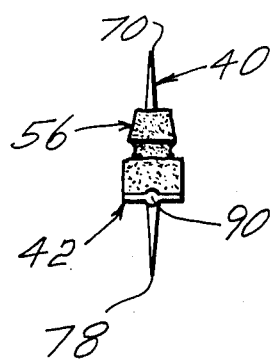
FIG. 9 is an end elevational view of the stub of the tooth after it has been removed from the dental stone, acutal size, and also illustrates the dowel pin.
Figure 10:
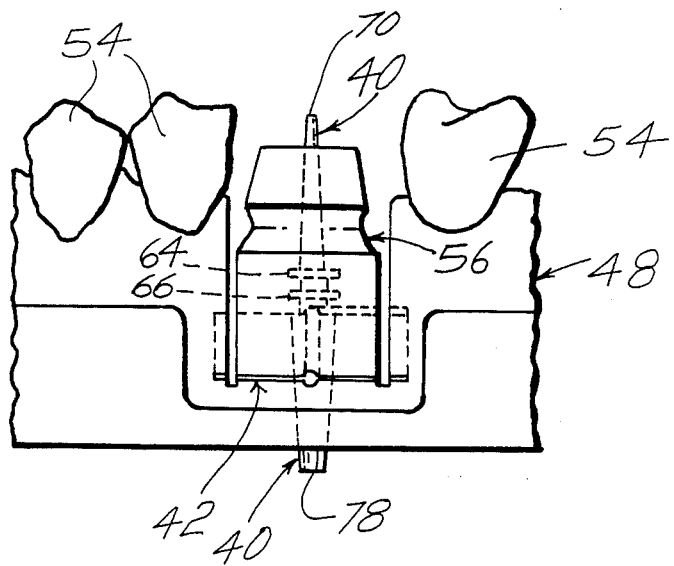
FIG. 10 is a fragmentary side elevational view illustrating the stone replica of the stub of the tooth with the sides of the stone removed and also illustrates the dowel pin and the guide of the stub of the tooth and with the stub of the tooth in position in the dental stone replica of the jaw and the teeth.
Figure 11:
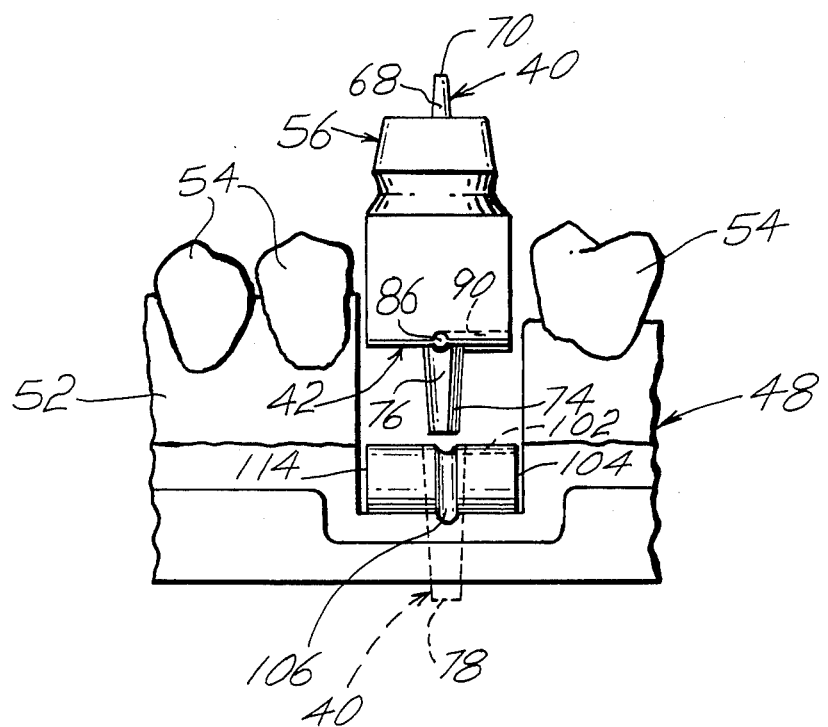
FIG. 11 is a fragmentary side elevational view of the dental stone replica of the gum between the teeth and also illustrates the dental stone replica of the stub of the tooth as lifted away from the dental stone and illustrates the dowel pin and the guide.
Figure 12:
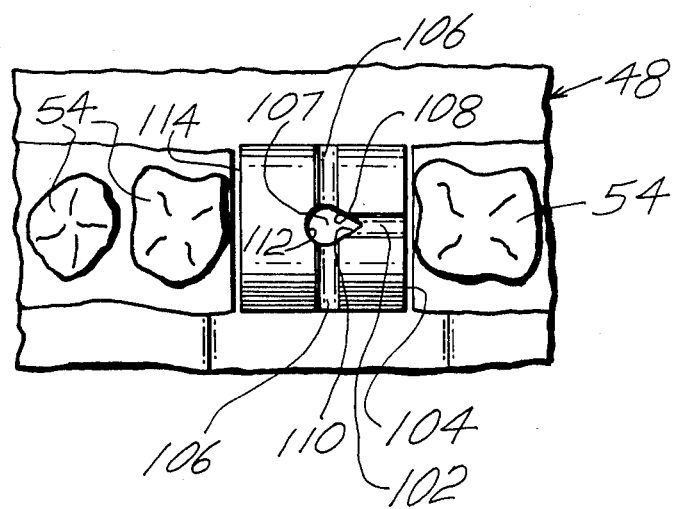
FIG. 12 is a fragmentary top plan view of the dental stone replica of the gum and the guide for the dental stone replica of the stub of the tooth.
Figure 13:
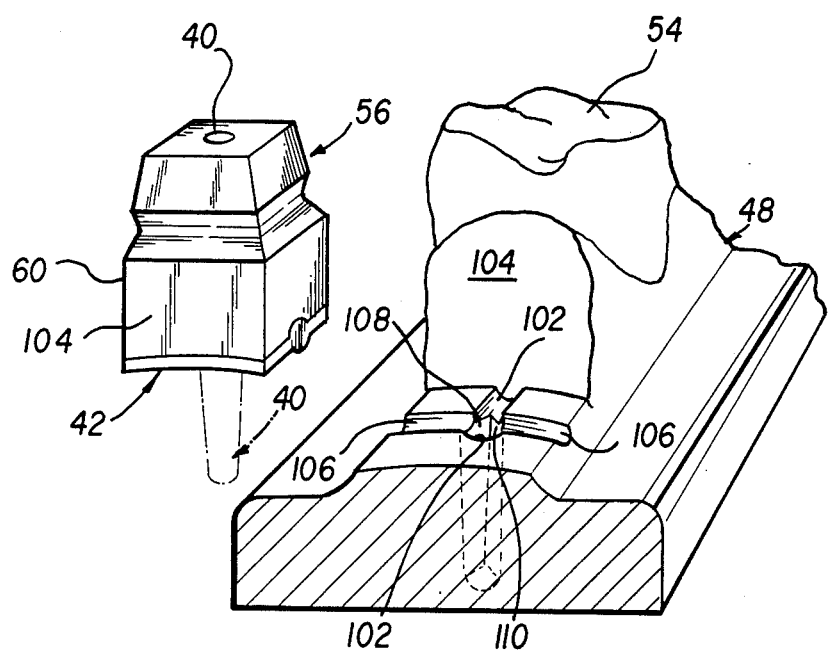
FIG. 13 is a fragmentary axonometric view illustrating the dental stone replica of the gum and the tooth and also the dental stone replica of the stub of the tooth with the stub of the tooth removed from the dental stone replica.
Figure 21:
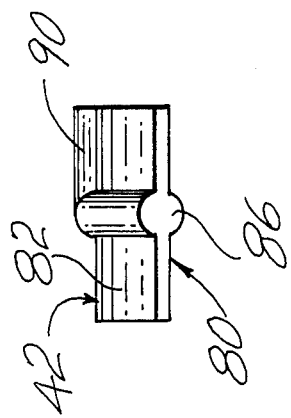
FIG. 21 is a end elevational view of the parting guide and it is to be understood that the end elevational view of the other end is the same as FIG. 21 except for reversal of the rib.
Figure 20:
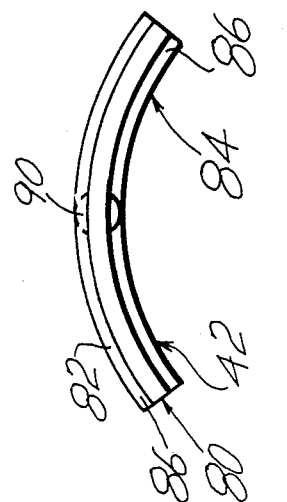
FIG. 20 is a second side elevational view of the parting guide and that side elevational view as opposed to the side elevational view of FIG. 19.
Figure 19:
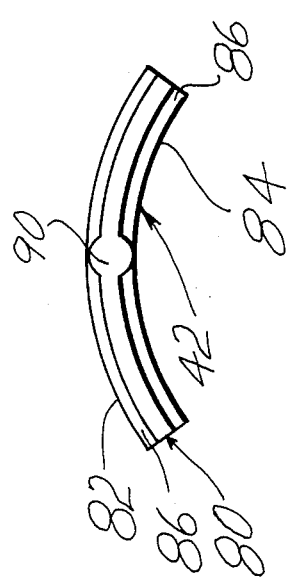
FIG. 19 is a first side elevational view of the parting guide.
Figure 23:
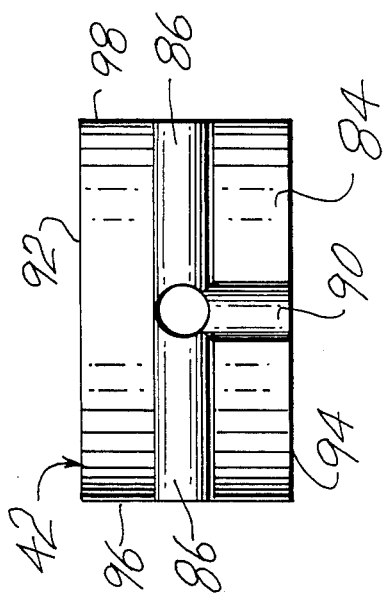
FIG. 23 is a bottom plan view of the parting guide.
Figure 22:
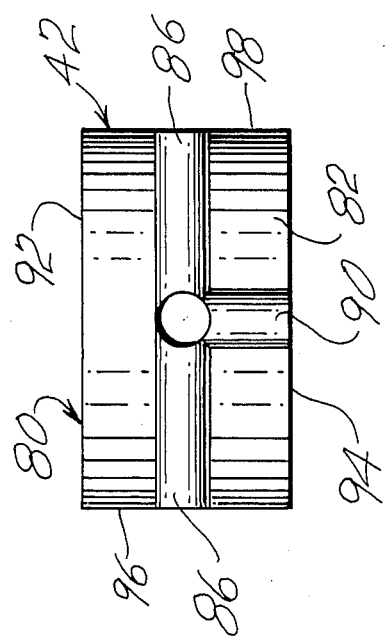
FIG. 22 is a top plan elevational view of the parting guide.

In FIG. 5 there is illustrated the castmodel 48 with the model tooth 56 removed. It is possible to see that the central half lateral guide 90 of the parting guide 42 left an impression 102 in the castmodel 48. The impression 102 is directed to the mesial cut 104 of the castmodel 48.

The raised central longitudinal guides 86 and 88 have left a groove 106 in the castmodel 48 and which groove 106 extends from the buccal side of the gum to the lingual side of the gum. The dowel pin has left a central passageway 107 in the castmodel 48.

Also, the flat face 72 has left a flat face 108 in the passageway 107 in the castmodel 48. The flat face 74 has left a flat face 110 in the castmodel 48. The curved face or curved part 76 of the dowel pin 40 has left a curved face 112 in the castmodel 48. The flat faces 108 and 110 are directed to the mesial cut 104. The curved face 102 is directed to the distal cut 114.

The reader is to remember that the plastic parting guide 42 is on the bottom of the model tooth 56 which has been removed from the castmodel 48.

FIGS. 6, 7, 8 and 9 are an illustration of the model tooth 56. That portion of the dowel pin 40 which extended beyond the model tooth 56 has been removed so that the dowel pin 40 is flush with the outer surface of the model tooth 56. There is illustrated the buccal wall 58 of the gum and also the lingual wall 60 of the gum. Further, there is illustrated the mesial cut 94 and the distal cut 114.

To repeat, the parting guide 42 is on the lower part of the model tooth 56. As the dental stone 44 did not adhere to the plastic parting guide 42 and as the parting guide 42 has been severed from the castmodel 48 by the mesial cut 104 and the distal cut 114 and also by the recesses in the buccal wall of the gum and the lingual wall of the gum the model tooth 56 can be removed from the castmodel 48. The dowel pin 40 may adhere to a degree to the castmodel 48. It may be necessary to gently tap that end of the dowel pin 40 which extends beyond the base 50 of the castmodel 48. With a gentle tap on the dowel pin 40 the model tooth 56 should readily be removed from the castmodel 48.

The model tooth 56 is to be removed from the castmodel 48. It is difficult to work on the model tooth 56 when in the castmodel 48. In regard to dental prosthetics on the model tooth 56 such as preparing a cap it is easier to work on the model tooth 56 when removed from the castmodel 48.

The cap on the model tooth 56 must mesh or align or fit with the corresponding tooth in the other jaw. The cap can be prepared and then positioned on the stub tooth in the mouth of the dental patient. The cap is prepared of a metal and isadhered to the stub tooth by means of an adhesive. If the cap is too large or does not fit with the corresponding tooth in the other jaw of the dental patient the dental patient has a sore jaw and is in considerable pain. Even if the cap is only a very small amount too large or has a high spot the dental patient suffers considerable pain and agony. Therefore, the cap for the stub tooth of the dental patient must be accurately and precisely prepared and made so that the dental patient is not in agony.

With the model tooth 56 removed from the castmodel 48 it is easier for the dental technician to prepare the cap. One prerequisite in the preparing of the cap for the model tooth 56 is that the tooth 56, after being removed from the castmodel 48, must be positioned again in the castmodel 48 as originally positioned. The positioning of tooth 56 and castmodel 48 can be achieved by the use of the parting guide 42 and also by use of the dowel pin 40. The parting guide 42 has raised central longitudinal guides 86 and 88 and half lateral guide 90. In the castmodel 48 there is a recess 106 corresponding to the longitudinal guide 88 and also a recess 102 corresponding to the lateral guide 90. In the model tooth 56 there is a recess corresponding to the longitudinal guide 86 and the half lateral guide 90. By placing the model tooth in the castmodel 48 the guides 86 and 88 and the half lateral guide 90 can mesh and be aligned by means of the appropriate recesses in the castmodel 48 and also in the model tooth 56.

In regard to the dowel pin 40 it is to be remembered that the dowel pin 40 has two flat faces 72 and 74 and a curved part 76. The two flat faces 72 and 74 have made corresponding flat faces 108 and 110 in the castmodel 48 and the curved part 76 or the curved surface 76 is made a corresponding curved surface 112 in the castmodel 48. The dowel pin 40 is definitely and permanently positioned in the model tooth 56. Therefore, the two flat face 72 and 4 and the curved surface 76 align the model tooth 56 with respect to the castmodel 48.

In this manner the model tooth 56 is definitely aligned and positioned in the castmodel 48 by means of the parting guide 52 and also by means of the dowel pin 40.

The plastic parting guide 42 does not adhere to the cured dental stone. As, previously, explained the perimeter of the parting guide 42 is severed. It is possible to tap on that part of the dowel pin 40 which extends below the castmodel 48. The model tooth 56 moves and the dowel pin is loosened from the castmodel 48 and also the parting guide 42 is loosened from the castmodel 48. This makes it possible to remove the model tooth 56 so that a cap can be prepared for the tooth 56. The cap can be prepared on the model tooth 56. From experience, after the dental technician has prepared the cap on the model tooth 56 the dentist will position the cap on the stub of the tooth in the mouth of the dental patient. The dentist, in order to secure a comfortable fit for the dental patient, will prepare the cap while the cap is on the stub of the tooth. Then, after the cap has been prepared by the dentist the cap can be adhered to the stub of the tooth by a dental adhesive.

Some of the objects and advantages of this invention are that it is possible to make a dentalmaster model with a removable dental tooth; to make a castmodel or a dental master model in less time than was previously possible; to make a castmodel of higher quality and more consistently favorable results than previously possible; to make a dental castmodel by a person of less skill than previously possible to use the combination of a dowel pin and a parting guide for aligning the removable replica of the model tooth from the dental castmodel; to provide a method and also an apparatus which can be performed by a person with a minimum of skill for positioning the dowel pin in the dental mastic prior to the pouring of the uncured dental stone; to provide a dowel pin which precludes the rotational movement of the removable model tooth from the dental castmodel; to provide a method and apparatus which eliminates the necessity of extensive technical skill in preparing a castmodel of a dental patient's oral cavity comprising a replica of the gum or gums and the teeth; and, to provide a method and an apparatus which requires only a single casting of the uncured dental stone in the negative of the dental patient's gum or gums and teeth.

In achieving these objects and advantages it is realized that the mastic 32 must retain the impression of the teeth and gum of the dental patient. As an example in explaining this invention the recess 38 in the mastic 32 may correspond to the stub of the tooth of the dental patient and which stub is to be capped. Also, the reader is to understand that the uncured dental stone 44 is in the recess 38 and which recess corresponds to the stub of the tooth of the dental patient. The model tooth 56 is the replica of the stub of the tooth of the dental patient and is the positive of the recess 38 in the mastic 32 and corresponds to the recess 38 and the negative or the mastic 32.

From the foregoing description it is seen that we have provided a castmodel of the dental patient's oral jaw wherein the castmodel comprises a base and a replica gum of the gum of said dental patient's oral jaw and a model tooth being a replica of a tooth of said dental patient; a parting guide in said castmodel; said parting guide being positioned at approximately the junction of said base and said replica gum; a dowel pin in said castmodel and in said model tooth and in said patient's gum; wherein said parting guide comprises a sheet of material having a first and a second surface; a longitudinal guide in said first surface and in said second surface; a lateral guide in said first surface and in said second surface; said dowel pin comprising a shank, a first end and a second end; a circumscribing ridge juxapositioned to the shank; said first end having two faces which join and form an edge; said longitudinal guide and said lateral guide being raised above said first surface and raised above said second surface; said first end tapering and having a larger cross-sectional dimension near the shank than at its outer end; and, said second end tapering and having a larger cross-sectional dimension near the shank than at its outer end; said parting guide having a plurality of sides; said longitudinal guide and said lateral guide being raised above said first surface and raised above said second surface; said pin extending beyond the surface of said base; said pin extending beyond the surface of said model tooth; said base being recessed on the outside of said replica gum in the vacinity of said model tooth; the outside of said patients gum being visible; said base being recessed on the inside of said replica gum in the vacinity of said model tooth; the inside edge of said patient's gum being visible; and, said model tooth being capable of being separated from the rest of said castmodel. Also, it is seen that we have provided a method for making a castmodel of a dental patient's oral jaw and said method comprising making a negative of said dental patient's oral jaw having a least one recess corresponding to a tooth; positioning a dowel pin in said recess; positioning a parting guide juxtapositioned to said recess; adding a flowable uncured dental stone to said negative to cover said recess and part of said dowel pin and, at least, part of said parting guide; and, allowing said uncured dental stone to cure to form said castmodel.

35 U.S.C. 101 states:
Whoever invents or discovers any new and useful process, machine, manufactur, or composition of matter, or any new and useful improvement thereof may obtain a patent therefor, subject to the conditions and requirements of this title.

35 U.S.C. 103 states:

A Patent may not be obtained though the invention is not identically disclosed or described as set forth in section 102 of this title, if the differences between the subject matter sought to be patented and the prior art are such that the subject matter as a whole would have been obvious at the time the invention was made to a person having ordinary skill in the art to which said subject matter pertains. Patentability shall not be negatived by the manner in which the invention was made.

We believe that this invention is new and unobvious. Before preparing this patent application we made patent searches. In the patent searches we did not find a parting guide such as a parting guide we teach and use. Also, we did not find a dowel pin such as we teach and use. In our invention we use a single pour of uncured dental stone to go into the negative of the dental patient's gum and teeth. This single pour of uncured dental stone covers most of the dowel pin and covers the parting guide. After the uncured dental stone has cured the dowel pin projects beyond the base of the castmodel 48 and also beyond the outer surface of the model tooth 56. In other words, the dowel pin 42 projects through the castmodel 48, including the model tooth 56, so that both ends of the dowel pin are outside of the castmodel 48. The dowel pin can be of metal. We consider that a dowel pin of plastic to have advantages. One of these advantages is that that part of the dowel pin extending beyond the outer surface of the model tooth 56 can easily be removed. The excess dowel pin 42 may be burned away or melted away or cut away or severed away. With a plastic dowel this can be easily and readily accomplished. With a metal dowel pin it is more difficult to remove that portion of the dowel pin extending beyond the outer surface of the model tooth 56. Another advantage of a plastic dowel pin is that a dowel pin of plastic is inexpensive and easy to make in a mold such as an injection mold. A metal dowel pin is more difficult and more costly to make than a plastic dowel pin.

We consider the invention to be useful as we can prepare a castmodel 48 of a dental patient with one pour instead of two pours. Also, with the parting guide it is possible to sever the perimeter of the parting guide from the castmodel so that the model tooth 56 can be removed from the castmodel 48. The parting guide and the dowel pin make it possible to align the model tooth 56 with the rest of the castmodel 48 when necessary. The model tooth 56 can be readily removed from the castmodel 48 so that the dental technician can use dental prosthetics for making a cap for the model tooth 56 and which cap can then be placed on the corresponding stub of a tooth of a dental patient.

From the foregoing and having presented our invention, what we claim is:

1. A curved parting guide for use in dental prosthetics, said parting guide comprising:
   a. a sheet of material having a convex surface and a concave surface;
   b. a longitudinal guide in said convex surface and in said concave surface; and,
   c. a lateral guide in said convex surface and in said concave surface.
2. A parting guide according to claim 1 and comprising:
   a. said longitudinal guide being centrally positioned; and,
   b. said lateral guide being centrally positioned.
3. A parting guide according to claim 1 and comprising:
   a. said parting guide having a plurality of sides.
4. A parting guide according to claim 1 and comprising:
   a. said longitudinal guide and said lateral guide being raised above said convex surface and raised above said concave surface;
   b. said sheet of material being rectangular and having four sides; and,
   c. sid sheet of material having one hole for receiving a pin.
5. A parting guide according to claim 1 and comprising:
   a. said longitudinal guide being centrally positioned;
   b. said lateral guide being centrally positioned;
   c. said longitudinal guide and said lateral guide being raised above said convex surface and raised above said concave surface; and,
   d. said sheet of material having one hole for receiving a pin.
6. A combination of a curved parting guide and a unitary dowel pin and comprising: said curved parting guide comprising:
   a. a sheet of material having a convex surface and a concave surface;
   b. a longitudinal guide in said convex surface and in said concave surface;
   c. a lateral guide in said convex surface and in said concave surface;
   d. said sheet of material having one hole for receiving a pin;
   e. a shank, a first end and a second end;
   f. a circumscribing ridge juxtapositioned to the shank;
   g. said first end having two faces which join and form an edge; and,
   h. said unitary dowel pin projecting through said hole in said parting guide and being positioned in said parting guide.
7. A combination according to claim 6 and comprising:
   a. said longitudinal guide being centrally positioned;
   b. said lateral guide being centrally positioned;
   c. said two faces of said unitary dowel pin being joined by a curved surface; and,
   d. said second end of said unitary dowel pin being of a circular cross-section.
8. A combination according to claim 7 and comprising:
   a. said longitudinal guide and said lateral guide being raised above said convex surface and raised above said concave surface;
   b. said first end of said unitary dowel pin tapering and having a larger cross-sectional dimension near the shank than at its outer end; and,
   c. said second end of said unitary dowel pin tapering and having a larger cross-sectional dimension near the shank than at its outer end.
9. A combination according to claim 8 and comprising:
   a. said parting guide having a plurality of sides.
10. A combination according to claim 9 and comprising:
    a. said longitudinal guide and said lateral guide being raised above said convex surface and being raised above said concave surface.
11. A combination of a negative, a curved parting guide and a unitary dowel pin, and comprising:

a. said negative having at least one recess corresponding to a tooth;
b. said unitary dowel pin projecting into said negative at said recess;
c. said unitary dowel pin comrpising a shank, a first end and a second end;
d. said curved parting guide comprising a sheet of material having a convex surface and a concave surface;
e. a longitudinal guide in said convex surface and in said concave surface;
f. a lateral guide in said convex surface and in said concave surface;
g. said sheet of material having one hole for receiving said dowel pin;
h. said unitary dowel pin projecting through said one hole in said unitary parting guide and being positioned in said parting guide; and,
i. said convex surface being closer to said recess than said concave surface.

12. A combination according to claim 11 and comprising:
a. a circumscribing ridge juxtapositioned to the shank; and,
b. said first end having two faces which join and form an edge.

13. A combination according to claim 12 and comprising:
a. said two faces joined by a curved surface;
b. said second end being of a circular cross-section;
c. said longitudinal guide being centrally positioned;
d. said lateral guide being centrally positioned;
e. said two faces joined by a curved surface; and,
f. said second end being of a circular cross-section.

14. A combination according to claim 13 and comprising:
a. said first end tapering and having a larger cross-sectional dimension near the shank than at its outer end;
b. said second end tapering and having a larger cross-sectional dimension near the shank than at its outer end;
c. said longitudinal guide and said lateral guide being raised above said convex surface and raised above said concave surface;
d. said first end tapering and having a larger cross-sectional dimension near the shank than at its outer end; and;
e. said second end tapering and having a larger cross-sectional dimension near the shank than at its outer end.

15. A combination according to claim 14 and comprising:
a. a dental casting stone in said negative;
b. said dental casting stone being in said recess and encompassing at least part of said unitary dowel pin and encompassing at least part of said curved parting guide; and,
c. said dental stone and said curved parting guide do not adhere to each other.

16. A combination according to claim 12 and comprising:
a. a dental casting stone in said negative;
b. said dental casting stone being in said recess and encompassing at least part of said unitary dowel pin and encompassing at least part of said curved parting guide; and,
c. said dental stone and said curved parting guide do not adhere to each other.

17. A castmodel of a dental patient's oral jaw, said castmoldel comprising:
a. a base and a replica gum of the gum of said dental patient's oral jaw and a model tooth being a replica of a tooth of said dental patient;
b. a curved parting guide in said castmodel;
c. said parting guide being positioned at approximately the junction of said base and said replica gum;
d. a unitary dowel pin in said castmodel and in aid model tooth and in said replica gum and in said parting guide and to project beyond said convex surface and to project beyond said concave surface;
e. said curved parting guide comprising a sheet of material having a convex surface and a concave surface;
f. a longitudinal guide in said convex surface and in said concave surface;
g. a lateral guide in said convex surface and in said concave surface;
h. a unitary pin comprising a shank, a first end and a second end;
i. a circumscribing ridge juxtapositioned to the shank;
j. said first end having two faces which join and form an edges; and,
k. the major part of said replica gum being on the outside of said concave surface of said parting guide.

18. A castmodel according to claim 17 and comprising:
a. said longitudinal guide being centrally positioned;
b. said lateral guide being centrally positioned;
c. said two faces joined by a curved surface; and,
d. said second end being of a circular cross-section.

19. A castmodel according to claim 18 and comprising:
a. said longitudinal guide and said lateral guide being raised above said convex surface and raised above said concave surface;
b. said first end tapering and having a larger cross-sectional dimension near the shank than at its outer end; and,
c. said second end tapering and having a larger cross-sectional dimension near the shank than at its outer end.

20. A castmodle according to claim 19 and comprising:
a. said parting guide having a plurality of sides.

21. A castmodel according to claim 19 and comprising:
a. said longitudinal guide and said lateral guide being raised above said convex surface and raised above said concave surface.

22. A castmodel according to claim 19 and comprising:
a. said pin extending beyond the surface of said base; and,
b. said pin extending beyond the surface of said model tooth.

23. A castmodel according to claim 19 and comprising:
a. said base being recessed on the outside of said replica gum in the vicinity of said model tooth;
b. the outside edge of said replica gum being visible;

c. said base being recessed on the outside of said replica gum in the vicinity of said model tooth; and;
d. the inside edge of said replica gum being visible.

24. A castmodel according to claim 23 and comprising:
a. said parting guide and said castmodel to not adhere to each other; and,
b. said model tooth being capable of being separated from the rest of said castmodel.

25. A castmodel according to claim 24 and comprising:
a. said pin extending beyond the surface of said base; and,
b. said pin extending beyond the surface of said model tooth.

26. A method for making a castmodel of a dental patient's oral jaw, said method comprising:
a. making a negative of said dental patient's oral jaw having at least one recess corresponding to a tooth;
b. positioning a unitary dowel pin in said recess;
c. positioning a curved parting guide justapositioned to said recess;
d. adding a flowable uncured dental stone to said negative to cover said recess and part of said unitary dowel pin, and, at least, part of said curved parting guide;
e. allowing said uncured dental stone to curve to form said castmodel;
f. selecting said parting guide and said dental stone to preclude said parting guide and said dental stone adhering to each other;
g. said curved parting guide comprising a sheet of material having a convex surface and a concave surface;
h. a longitudinal guide in said convex surface and in said concave surface;
j. a lateral guide in said convex surface and in said concave surface;
j. said unitary dowel pin comprising a shank, a first end and a second end;
k. a circumscribing ridge juxtapositioned to the shank;
l. said first end having two faces which join and form an edge;
m. said convex surface being closer to said recess than said concave surface; and,
n. said flowable uncured dental zone in rising upwardly in said recess and in said negative contacts said convex surface prior to contacting said concave surface and then rises to cover at least part of said concave surface.

27. A method according to claim 26 and comprising:
a. said longitudinal guide being centrally positioned;
b. said lateral guide being centrally positioned;
c. said two faces joined by a curved surface; and,
d. said second end being of a circular cross-section.

28. A method according to claim 27 and comprising:
a. said parting guide having a plurality of sides;
b. said first end tapering andhaving a larger cross-sectional dimension near the shank than at its outer end; and,
c. said second end tapering and having a larger cross-sectional dimension near the shank than at its outer end.

29. A method according to claim 28 and comprising:
a. said longitudinal guide and said lateral guide being raised above said convex surface and raised above said concave surface; and, b. said sheet of material being rectangular and having four sides.

30. A castmodel of a dental patient's oral jaw prepared by the process comprising:
a. making a negative to said dental patient's jaw having at least one recess corresponding to a tooth;
b. positioning a unitary dowel pin in said recess;
c. positioning a parting guide juxtapositioned to said recess;
d. said parting guide being curved and having a concave surface and a convex surface;
e. juxtapositioning said convex surface near said recess and positioning said concave surface above said convex surface
f. positioning said dowel pin in said parting guide;
g. adding a flowable uncured dental stone to said negative to cover said recess and part of said dowel pin and, at least, part of said parting guide by rising upwardly in said recess and in said negative to contact said convex surface prior to contacting said concave surface and then to cover at least part of said concave surface;
h. allowing said uncured dental stone to cure to form said castmodel; and,
i. and selecting said parting guide and said dental stone to preclude said parting guide and said dental stone adhering to each other.

31. A castmodel according to claim 30 and comprising:
a. said parting guide comprising a sheet of material having a first surface identified as said convex surface and a second surface identified as said concave surface;
b. a longitudinal guide in said first surface and in said second surface;
c. a lateral guide in said first surface and in said second surface;
d. said unitary dowel pin comprising a shank, a first end and a second end;
e. said unitary dowel pin comprising a circumscribing ridge juxtapositioned to the shank; and,
f. said first end having two faces which join and form an edge.

32. A castmodel according to claim 31 and comprising:
a. said longitudinal guide being centrally positioned;
b. said lateral guide being centrally positioned;
c. said two faces of said unitary dowel pin being joined by a curved surface; and,
d. said second end of said unitary dowel pin being of a circular cross-section.

33. A castmodel according to claim 32 and comprising:
a. said parting guide having a plurality of sides;
b. said first end tapering and having a larger cross-sectional dimension near the shank than at its outer end;
c. said second end tapering and having a larger cross-sectional dimension near the shank than at its outer end; and,
d. with said dowel pin in said parting guide said parting guide and said dowel pin being continuous.

34. A castmodel according to claim 33 and comprising:
a. said longitudinal guide and said lateral guide being raised above said first surface and raised above said second surface; and, b. said sheet of material being rectangular and having four sides.

35. A castmodel according to claim 30 and comprising:
   a. said castmodel comprising a base and a replica gum of the gum of said dental patient's oral jaw and a model tooth being a replica of a tooth of said dental patient;
   b. removing some of said base on the outside of said replica gum in the vicinity of said model tooth to reveal the outside edge of said patient's gum; and,
   c. removing some of said replica gum in the vicinity of said model tooth to reveal the inside edge of said patient's gum.

36. A cast model according to claim 35 and comprising:
   a. severing the distal side of said model tooth and said parting guide from said castmodel; and,
   b. severing the mesial side of said model tooth and said patient's gum from said castmodel.

37. A castmodel according to claim 36 and comprising:
   a. removing said model tooth from said castmodel.

* * * * *